United States Patent [19]

Bell et al.

[11] Patent Number: 4,714,787

[45] Date of Patent: Dec. 22, 1987

[54] PRODUCTION OF ETHERS FROM LINEAR OLEFINS

[75] Inventors: Weldon K. Bell, Pennington; Werner O. Haag, Lawrenceville, both of N.J.

[73] Assignee: Mobil Oil Corporation, New York, N.Y.

[21] Appl. No.: 772,090

[22] Filed: Sep. 3, 1985

[51] Int. Cl.$^4$ ............................................. C07C 41/06
[52] U.S. Cl. ...................................................... 568/697
[58] Field of Search ............................................ 568/697

[56] References Cited

U.S. PATENT DOCUMENTS

| | | | |
|---|---|---|---|
| 2,067,385 | 1/1937 | Evans et al. | 568/678 |
| 3,966,586 | 6/1976 | Owen et al. | 568/697 |
| 4,042,633 | 8/1977 | Woods | 568/697 |
| 4,175,210 | 11/1979 | Selwitz et al. | 568/697 |
| 4,182,914 | 1/1980 | Imaizumi | 568/697 |
| 4,262,145 | 4/1981 | Selwitz et al. | 568/689 |
| 4,418,219 | 11/1983 | Hanes et al. | 568/697 |
| 4,590,294 | 5/1986 | Ballantine et al. | 568/697 |

FOREIGN PATENT DOCUMENTS

| | | | |
|---|---|---|---|
| 45618 | 2/1982 | European Pat. Off. | |
| 55045 | 6/1982 | European Pat. Off. | 568/697 |
| 133661 | 1/1979 | Fed. Rep. of Germany | 568/697 |
| 25345 | 2/1984 | Japan | 568/697 |

*Primary Examiner*—Howard T. Mars
*Attorney, Agent, or Firm*—Alexander J. McKillop; Michael G. Gilman; L. G. Wise

[57] ABSTRACT

A catalytic process is provided for the manufacture of ethers by reacting a linear monoolefin with a primary or secondary alcohol having up to 4 carbon atoms. The process selectively forms methyl isopropyl ether from a propylene feed and methanol by contact with a zeolite such as Zeolite Beta or ZSM-5, or by contact with a macroreticular sulfonated ion-exchange resin.

4 Claims, 3 Drawing Figures

ZSM-5

AMBERLYST 15

CONTINUOUS REACTOR, ZEOLITE BETA

PRODUCTION OF ETHERS FROM LINEAR OLEFINS

FIELD OF THE INVENTION

This invention is concerned with the manufacture of ethers from linear monoolefins. In particular it is concerned with the manufacture of ethers by the catalytic reaction of linear monoolefins with primary or secondary alcohols having up to four carbon atoms. It is further concerned with the manufacture of methyl isopropyl ether.

BACKGROUND OF THE INVENTION

U.S. Pat. No. 4,262,145 to Selwitz et al. discloses the catalytic reaction of a branched olefin such as isobutylene, 2-methylpentene-2, 2-methylbutene-2 and 2,3-dimethyloctene-2 with a lower alkanol such as methanol to form a mixed ether such as methyl tert-butyl ether. The catalyst disclosed is silicotungstic acid.

There is a need for an efficient catalytic process to manufacture ethers from linear monoolefins, thereby augmenting the supply of high-octane blending stock for gasoline. The lower molecular weight ethers, such as methyl isopropyl ether, are in the gasoline boiling range and are known to have a high blending octane number. In addition, by-product propylene is usually available in a fuels refinery. The petrochemicals industry also produces linear olefin streams in the $C_3$ to $C_{15}$ molecular weight range, and the conversion of such streams or fractions thereof to ethers can provide products useful as solvents and as blending stocks for fuels.

BRIEF SUMMARY OF THE INVENTION

This invention provides a catalytic process for selectively reacting one or more linear monoolefins with a primary or secondary lower molecular weight alcohol to form the corresponding ethers. The active acidic catalyst component is selected from the group consisting of sulfonated ion-exchange resins and crystalline silicates having a pore size greater than 5 A.U. Of the crystalline silicates, those preferred include crystalline zeolites having a silica to alumina mol ratio greater than about 12. In a particularly preferred embodiment, methanol and propylene are reacted to selectively form methyl isopropyl ether (MIPE).

DETAILED DESCRIPTION AND BEST MODE

Figure 2:
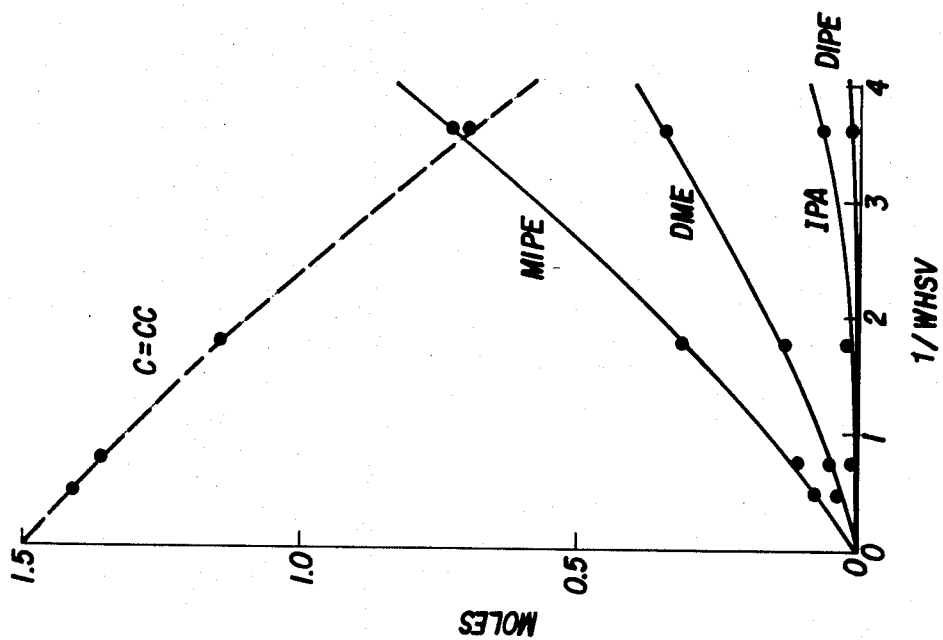
FIG. 2. Batch conversion, ZSM-5 catalyst.

The process of this invention is based on the discovery that linear monoolefins, under the proper reaction conditions, react in the presence of a solid insoluble acid catalyst with a low molecular weight primary or secondary monohydric alcohol to selectively produce the ethers.

Linear monoolefins and mixtures thereof useful in the process of this invention include, broadly, those having 3 to 15 carbon atoms, and these have the structure $$R_1-CH=CH-R_2$$

wherein $R_1$ and $R_2$ individually are hydrogen or n-alkyl groups and the total carbon atoms in $R_1$ plus $R_2$ is from 1 to 13. In a preferred embodiment of the present invention, the preferred linear olefins are those having 3 to 5 carbon atoms, i.e. the total carbon atoms in $R_1$ plus $R_2$ is 1 to 3. Particularly preferred is propylene.

Although the hydrocarbon feed to the process may be substantially pure linear olefin (i.e. greater than 90 wt % of olefin), it is a feature of the invention that the reaction proceeds well in the presence of paraffin. For example, the by-product liquid propane gas (LPG) recovered from catalytic cracking in a typical petroleum refinery and containing 20-80 wt % propylene mixed with propane can be used as feed. Branched olefins such as isobutylene may be present up to about 10 mol % of the total olefin content of the feed. Under the process conditions of this invention, branched olefins are very rapidly converted to higher boiling oxygenates or oligomers which if desired, may readily be separated from the feed or the ether products. Small amounts of dienes, such as up to about 2 mol% of the olefin content of the hydrocarbon feed, also may be present.

The alcohol to be reacted with the linear olefin is any primary or secondary alcohol having up to 4 carbon atoms. These include the primary alcohols methanol, ethanol, n-propanol, n-butanol and isobutanol; and the secondary alcohols isopropanol and sec-butanol. The primary alcohols are preferred, with methanol being particularly preferred.

The process of this invention may be conducted batchwise, as will be illustrated by Examples 1 and 2. However, it is generally advantageous, and therefore preferred, to conduct the process as a continuous operation. Since the reaction is exothermic, temperature control is facilitated by a continuous cascade operation with two or more reactors in sequence and with interstage cooling. Operable reaction conditions are given in Table I. The weight hourly space velocity (WHSV) referred to in Table I and elsewhere herein, unless explicitly stated to be otherwise, is based on reactants, i.e. the total weight of linear olefin plus alcohol divided by the total weight of binder-free insoluble acid catalyst per hour. The corresponding contact times, of course, apply to batch conversions.

TABLE I

| | REACTION CONDITIONS | | | |
|---|---|---|---|---|
| | Mol Ratio Alcohol/Olefin | Temp., °C. | Pressure Atm, Total | WHSV $Hr^{-1}$ |
| Broad | 0.1–10 | 50–300 | 1.0–300 | 0.05–50 |
| Preferred | 0.3–3 | 80–250 | 5–200 | 0.2–20 |
| Most Preferred | 0.5–2 | 100–210 | 10–100 | 0.5–10 |

The principal ether product or products produced depends on the linear olefin and the alcohol charged. In the case of methanol and propylene, for example, the principal reaction product is methyl isopropyl ether. With butene-1 or the cis- or trans-butene-2, methyl sec-butyl ether is formed. In brief, the ethers formed are those predicted by the Markovnikov rule for addition to the double bond of the linear olefin. In the case of the higher molecular weight linear monoolefins, or mixtures of olefins, the principal reaction product is a mixture of such ethers.

The principal by-products formed in the conversion is the ether and water resulting from the autocondensation of the alcohol charged. Other by-products include alcohol resulting from the hydration of the linear monoolefin, and the ether formed by the self-condensation of the latter alcohol. Also formed is a small amount of hydrocarbon believed to be the oligomer of the olefin charged. This hydrocarbon by-product appears to account for substantially less than 5 wt % of the total olefin converted under moderate temperatures, such as at a temperature not higher than about 160° C.

EXAMPLES

This invention will now be illustrated by examples. Obviously many modifications and variations of the process as illustrated by the examples can be made without departing from the spirit and scope of the invention, which scope is to be determined by this entire specification including the appended claims. In the tables which follow, and sometimes elsewhere, products and by-products will be abbreviated as follows: dimethyl ether (DME); isopropyl alcohol (IPA); methyl isopropyl ether (MIPE); and diisopropyl ether (DIPE).

EXAMPLE 1

This example illustrates a batch operation wherein methanol and propylene are converted to methyl isopropyl ether.

Figure 1:
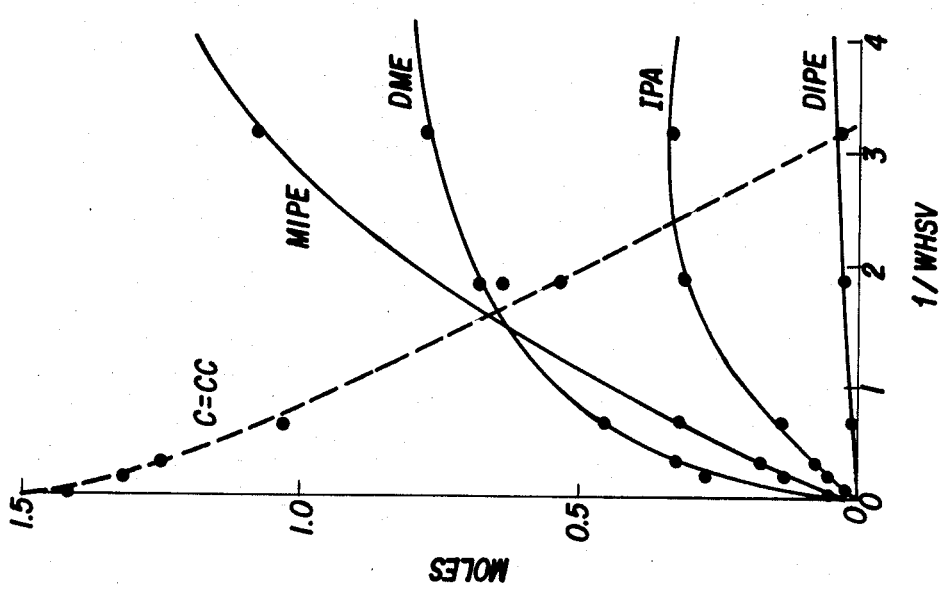
FIG. 1. Batch conversion, Amberlyst 15 catalyst.

A 50 gram sample of Amberlyst 15 in the hydrogen form was charged to a 300 ml stirred autoclave, purged in helium, and brought to about 120° C. in flowing helium at atmospheric pressure. The autoclave was isolated and 3.0 mols of methanol were added followed by the addition of 1.5 mols of propylene. Periodically temperature and pressure were recorded and the liquid contents of the autoclave were sampled by withdrawing 1 to 2 gram quantities through an internal filtered dip-tube. Samples were analyzed by GC-TCD using a temperature programmed Porapak-QS column (60° C. to 240° C. at 10° C./min.). All major components were identified by GC-MS (50 m DB 1 column). MIPE (methyl isopropyl ether) was also verified by H-NMR. Data work-up assumed that water, methanol, isopropanol, MIPE and DIPE ratios in the liquid sample represented those in the autoclave. Neglecting hydrocarbons, the product distributions and conversions were calculated from the charge composition, product stoichiometry, and the above ratios. Product distributions for various contact times are given in Table II and in FIG. 1 of the drawing.

TABLE II
BATCH PRODUCTION OF MIPE
Catalyst: 50 g Amberlyst-15

| Charge: 1.5 mols Propylene + 3.0 mols Methanol | | | | | | | |
|---|---|---|---|---|---|---|---|
| Hours | 0.20 | 0.53 | 0.97 | 2.00 | 6.03 | 10.60 | 25.28 |
| Temp, °C. | 124 | 118 | 119 | 128 | 128 | 128 | 128 |
| PSIG | 750 | 640 | 560 | 540 | 500 | 440 | 540 |
| WHSV* | 15.90 | 6.01 | 3.29 | 1.59 | 0.53 | 0.30 | 0.13 |
| REACTOR CONTENTS, MOLS | | | | | | | |
| Propylene | 1.43 | 1.32 | 1.25 | 1.03 | 0.53 | 0.03 | ~0 |
| Methanol | 2.22 | 2.33 | 2.18 | 1.77 | 1.01 | 0.41 | 0.18 |
| Water | 0.34 | 0.22 | 0.25 | 0.32 | 0.36 | 0.40 | 0.41 |
| DME | 0.37 | 0.27 | 0.33 | 0.45 | 0.68 | 0.76 | 0.76 |
| IPA | 0.03 | 0.05 | 0.07 | 0.14 | 0.31 | 0.33 | 0.28 |
| MIPE | 0.05 | 0.13 | 0.17 | 0.33 | 0.63 | 1.07 | 1.30 |
| DIPE | 0.00 | 0.00 | 0.00 | 0.00 | 0.01 | 0.03 | 0.08 |

*WHSV shown is calculated.

EXAMPLE 2

Example 1 was repeated but 50 grams of extrudate consisting of 65% ZSM-5 having a silica to alumina ratio of 70:1 and 35% alumina binder was substituted for the Amberlyst 15. The ZSM-5 was in the hydrogen form.

The results are summarized Table III and FIG. 2 of the drawing.

TABLE III
BATCH PRODUCTION OF MIPE
Catalyst: 50 g ZSM-5 EXTRUDATE

| Charge: 1.5 mols Propylene + 3.0 mols Methanol | | | | | | | |
|---|---|---|---|---|---|---|---|
| Hours | 0.66 | 1.50 | 2.25 | 5.58 | 11.50 | 18.80 | 23.80 |
| Temp, °C. | 124 | 123 | 127 | 134 | 115 | 112 | 120 |
| PSIG | 540 | 560 | 610 | 450 | 400 | 580 | 540 |
| WHSV* | 7.42 | 3.27 | 2.18 | 0.88 | 0.43 | 0.26 | 0.21 |
| REACTOR CONTENTS, MOLS | | | | | | | |
| Propylene | 1.36 | 1.41 | 1.38 | 1.16 | 0.70 | 0.07 | 0.12 |
| Methanol | 2.75 | 2.85 | 2.79 | 2.42 | 1.58 | 0.94 | 0.39 |
| Water | 0.05 | 0.03 | 0.05 | 0.11 | 0.28 | 0.27 | 0.52 |
| DME | 0.07 | 0.04 | 0.05 | 0.13 | 0.34 | 0.38 | 0.76 |
| IPA | 0.02 | 0.01 | .00 | 0.02 | 0.06 | 0.10 | 0.20 |
| MIPE | 0.11 | 0.08 | 0.11 | 0.32 | 0.73 | 1.30 | 1.09 |
| DIPE | 0.01 | .00 | .00 | .00 | .00 | 0.02 | 0.04 |

*WHSV shown is calculated.

EXAMPLES 3–7

Examples 3–7 illustrate the present invention with a continuous flow, flooded reactor, for the conversion of propylene and methanol to MIPE with different catalysts. In all of these examples the propylene and methanol were fed in equimolar ratio to an up-flow fixed bed reactor (20 mm I.D that was charged with 18 to 30 grams of catalyst diluted with sand to bring bed volume to 70 cc (except 43 cc for Amberlyst). ISCO (continuous positive displacement) pumps fed methanol and propylene (at 1200 psi) in a molar ratio of 1:1. The reaction conditions were about 160° C. (150° C. for Amberlyst), 1000 psig, and WHSV's of from 3 to 0.1. System pressure was maintained by a back pressure regulator. Liquid product condensed at system pressure and 20° C. was collected at atmospheric conditions. Gas flows were measured with a wet test meter. Analysis of products was by gas chromatograph (thermal conductivity detector) using a 6 foot Porapak-QS column temperature programmed from 70° C. to 240° C.

EXAMPLE 3

In this example the catalyst used was 65 wt % Zeolite Beta in 35 wt % alumina binder. The zeolite had a silica to alumina ratio of 37:1. The zeolite was in the hydrogen form. The results are shown in Table IV.

TABLE IV
CONTINUOUS REACTOR, EXAMPLE 3

| Catalyst - 18.2 grams Zeolite Beta Extrudate | | | | | |
|---|---|---|---|---|---|
| Hr on Stream | 2.5 | 24.3 | 28.0 | 48.0 | 50.2 |
| Temp, °C. | 163 | 160 | 161 | 163 | 163 |
| WHSV | 3.70 | 0.12 | 1.23 | 0.37 | 3.70 |
| CONVERSION BASED ON PRODUCTS | | | | | |
| Propylene | 54.18 | 90.75 | 74.65 | 79.08 | 47.63 |
| Methanol | 67.02 | 85.80 | 85.07 | 90.06 | 65.24 |
| PRODUCT STREAM, WT % | | | | | |
| Water | 1.49 | 5.24 | 2.10 | 1.05 | 0.81 |
| Propylene | 25.71 | 4.61 | 13.24 | 11.97 | 31.81 |
| Methanol | 14.55 | 6.62 | 7.26 | 4.23 | 13.72 |
| DME | 6.77 | 10.28 | 13.13 | 8.09 | 4.58 |
| IPA | 2.06 | 3.59 | 4.02 | 4.36 | 1.55 |
| MIPE | 46.61 | 59.40 | 53.47 | 62.72 | 44.81 |
| DIPE | 1.72 | 7.16 | 5.31 | 5.57 | 1.72 |
| Other* | 1.09 | 3.09 | 1.47 | 2.01 | 0.99 |

*"Other" represents by-products, probably propylene oligomers and their oxygenated derivatives.

EXAMPLE 4

In this example 30 grams of extrudate consisting of 65 wt % ZSM-5 having a silica to alumina mol ratio of 70:1 and 35 wt % of alumina binder was used. The zeolite was in the hydrogen form. The results are summarized in Table V.

TABLE V
CONTINUOUS REACTOR, EXAMPLE 4

Catalyst - 30 grams ZSM-5 extrudate

| Hr on Stream | 1.5 | 23.5 | 27.8 | 47.8 |
|---|---|---|---|---|
| Temp, °C. | 164 | 162 | 162 | 162 |
| WHSV | 3.00 | 0.10 | 1.00 | 0.30 |
| CONVERSION BASED ON PRODUCTS | | | | |
| Propylene | 28.00 | 86.84 | 39.65 | 62.90 |
| Methanol | 47.43 | 86.29 | 60.31 | 75.22 |
| PRODUCT STREAM, WT % | | | | |
| Water | 2.14 | 3.21 | 1.75 | 1.79 |
| Propylene | 42.67 | 6.42 | 35.84 | 20.13 |
| Methanol | 20.98 | 6.87 | 15.94 | 11.40 |
| DME | 6.02 | 13.25 | 6.38 | 8.63 |
| IPA | 3.30 | 7.04 | 3.49 | 3.24 |
| MIPE | 24.43 | 57.41 | 35.51 | 52.26 |
| DIPE | 0.33 | 5.32 | 0.86 | 2.04 |
| Other* | 0.14 | 0.48 | 0.23 | 0.51 |

EXAMPLE 5

In this example 31 grams of extrudate consisting of 65 wt % ZSM-12 having a silica to alumina mol ratio of 73:1 and 35 wt % alumina binder was charged to the reactor. The zeolite was in the hydrogen form. The results are summarized in Table VI.

TABLE VI
CONTINUOUS REACTOR, EXAMPLE 5

Catalyst - 31 grams ZSM-12 extrudate

| Hr on Stream | 1.6 | 24.5 | 28.2 | 48.0 | 53.7 |
|---|---|---|---|---|---|
| Temp, °C. | 161 | 161 | 162 | 162 | 162 |
| WHSV | 3.00 | 0.10 | 1.00 | 0.30 | 0.30 |
| CONVERSION BASED ON PRODUCTS | | | | | |
| Propylene | 14.05 | 79.51 | 30.59 | 39.89 | 35.17 |
| Methanol | 21.25 | 74.95 | 57.95 | 67.13 | 69.55 |
| PRODUCT STREAM, WT % | | | | | |
| Water | 2.56 | 3.41 | 1.40 | 2.52 | 2.36 |
| Propylene | 50.49 | 9.52 | 45.31 | 35.69 | 38.6 |
| Methanol | 30.78 | 13.25 | 14.50 | 13.22 | 12.54 |
| DME | 2.16 | 11.45 | 4.90 | 8.82 | 11.02 |
| IPA | 1.38 | 4.42 | 1.95 | 3.67 | 3.64 |
| MIPE | 12.26 | 54.87 | 30.45 | 34.09 | 30.79 |
| DIPE | 0.21 | 2.29 | 0.99 | 1.25 | 0.75 |
| Other | 0.16 | 0.79 | 0.50 | 0.73 | 0.29 |

EXAMPLE 6

In this example 20 grams of Amberlyst 15 macroreticular ion-exchange resin, purchased from the Rohm & Haas Company, Philadelphia, Pa. was charged to the reactor. The resin was in the acid form. The results are summarized in Table VII.

TABLE VII
CONTINUOUS REACTOR, EXAMPLE 6

Catalyst - 20 grams Amberlyst 15

| Hr on Stream | 1.2 | 22.3 | 25.6 | 28.2 | 47.0 |
|---|---|---|---|---|---|
| Temp, °C. | 152 | 153 | 156 | 157 | 151 |
| WHSV | 3.00 | 0.30 | 1.00 | 6.00 | 0.30 |
| CONVERSION BASED ON PRODUCTS | | | | | |
| Propylene | 65.29 | 82.91 | 78.94 | 53.82 | 86.95 |
| Methanol | 82.83 | 96.18 | 92.28 | 93.73 | 95.86 |
| PRODUCT STREAM, WT % | | | | | |
| Water | 1.84 | 1.18 | 1.92 | 0.69 | 1.13 |

TABLE VII-continued
CONTINUOUS REACTOR, EXAMPLE 6

| Propylene | 19.54 | 9.82 | 11.54 | 30.99 | 7.28 |
|---|---|---|---|---|---|
| Methanol | 7.39 | 1.58 | 3.46 | 2.03 | 1.81 |
| DME | 10.32 | 11.43 | 12.37 | 8.19 | 11.47 |
| IPA | 6.83 | 8.10 | 6.49 | 4.86 | 6.72 |
| MIPE | 49.21 | 55.2 | 55.85 | 43.96 | 59.83 |
| DIPE | 4.74 | 11.72 | 7.74 | 8.56 | 11.01 |
| Other* | 0.13 | 0.97 | 0.62 | 0.71 | 0.77 |

EXAMPLE 7

In this example 20 grams of Ultra Stable Zeolite Y, purchased from the Davison Chemical Division, W. R. Grace & Co., Baltimore, Maryland, was charged to the reactor in the hydrogen form. The results are summarized in Table VIII.

TABLE VIII
CONTINUOUS REACTOR, EXAMPLE 7

Catalyst - 20 grams Ultra Stable Zeolite Y

| Hr on Stream | 1.5 | 23.9 | 26.5 | 48.0 | 52.7 |
|---|---|---|---|---|---|
| Temp, °C. | 161 | 161 | 161 | 161 | 161 |
| WHSV | 3.00 | 0.10 | 1.00 | 0.30 | 1.00 |
| CONVERSION BASED ON PRODUCTS | | | | | |
| Propylene | 4.20 | 45.19 | 11.02 | 24.01 | 10.29 |
| Methanol | 12.57 | 54.64 | 35.25 | 49.73 | 27.68 |
| PRODUCT STREAM, WT % | | | | | |
| Water | 0.83 | 3.11 | 2.22 | 2.40 | 1.73 |
| Propylene | 55.37 | 25.34 | 60.17 | 44.01 | 54.29 |
| Methanol | 36.99 | 24.42 | 20.31 | 21.20 | 28.43 |
| DME | 2.59 | 11.60 | 4.78 | 8.83 | 4.89 |
| IPA | 0.23 | 4.17 | 2.13 | 2.99 | 1.12 |
| MIPE | 3.97 | 30.74 | 10.2 | 20.11 | 9.45 |
| DIPE | 0.02 | 0.56 | 0.17 | 0.39 | 0.06 |
| Other* | 0.00 | 0.06 | 0.03 | 0.08 | 0.03 |

Figure 3:
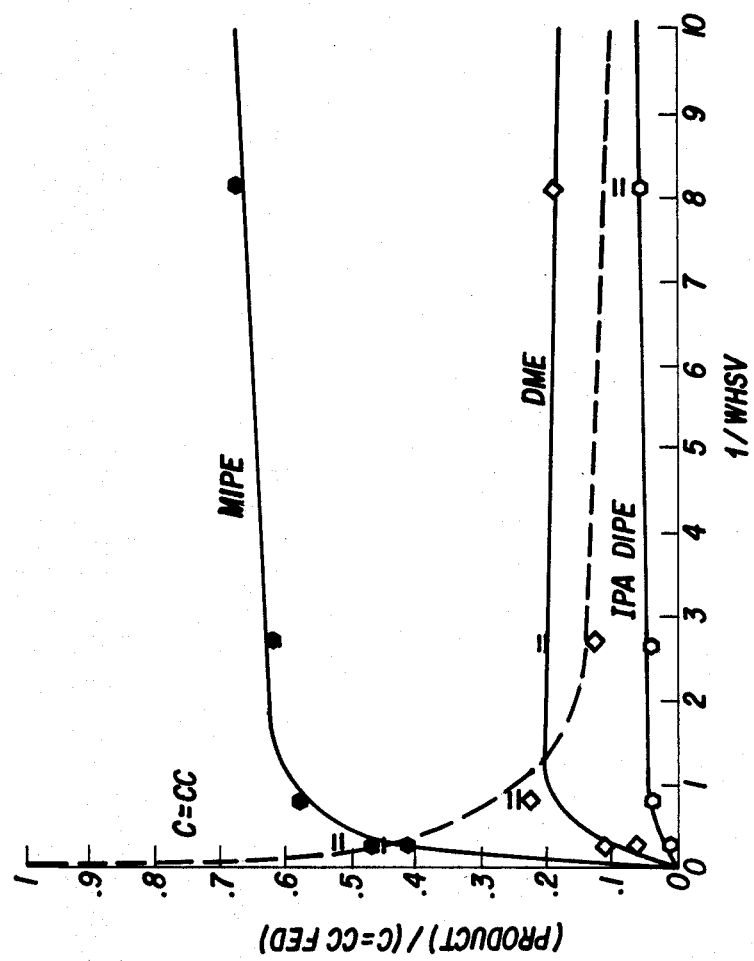
FIG. 3. Continuous Reactor, Zeolite Beta catalyst.

As will be evident from the foregoing examples, the principal reaction products from propylene and methanol are methyl isopropyl ether and dimethyl ether. This is clearly brought out in Example 3 with the Zeolite Beta catalyst, and with the graphical representation of the date in FIG. 3 of the drawing.

A particularly preferred embodiment of this invention utilizes a hydrocarbon feed consisting of about 20 to 100 wt % propylene and 0-80 wt % propane, and reacts this feed with methanol. The product formed is separated into a fraction comprising methyl isopropyl ether useful as a gasoline blending component. Unreacted propylene, methanol, and by-product dimethyl ether together with up to one mol of water per mol of ether, either individually or in any combination, can be combined with fresh feed and recycled to the process.

In another embodiment of this invention, it is contemplated to feed dimethyl ether and about a stoichiometric amount of water to form the requisite methanol in situ.

The solid, insoluble acidic catalysts useful in the present invention will now be described in detail. The term "acidic catalyst" as used herein is a solid which, in the proper form, is capable of catalyzing one or more reactions recognized in the art as proceeding by an acid-catalyzed mechanism. Such reactions include the dehydration of alcohols, cracking of paraffins, isomerization of alkylaromatic hydrocarbons and dealkylation of isopropylbenzene.

Sulfonated, cross-linked polystyrene resins are known and recognized to function as acid catalysts when in the hydrogen form. These resins are extensively used for water softening, and are manufactured and sold by several organizations under the names Dowex 50, Amberlite IR-120 and Ionac C-240. Particularly useful as catalyst and preferred for the purpose of this invention is Amberlyst 15, a porous (macroreticular) highly cross-linked sulfonated copolymer of styrene and divinylbenzene. This product is sold by Rohm & Haas, Philadelphia, Pa.

The crystalline silicates referred to herein are those porous, crystalline solids that have highly ordered, robust three-dimensional framework structures as evidenced by well-defined and reproducible X-ray diffraction patterns which are distinctive for the different framework structures. The ordered structures contain intracrystalline micropores, i.e. pores of molecular dimensions, regularly disposed in the crystal lattice and readily distinguishable from the much larger extracrystalline pores formed by agglomerates of microcrystals. Because of their intracrystalline nature, these pores are very uniform and, when free of occluded matter, selectively sorb only those molecules having a critical diameter that can be accomodated by the pore size of the particular mineral in question. Such microporous crystals are often referred to as "molecular sieves". The terms "pores" and "porous", as used herein, refers to the intracrystalline micropores unless explicitly stated to be otherwise.

The three-dimensional frameworks of the crystalline microporous crystals useful herein are formed by one or more tetrahedrally bonded elements linked together by covalent bonds to oxygen atoms. Such structures are found in nature as aluminosilicate deposits such as erionite and mordenite, although synthetic minerals of this type may contain other elements in place of some or all of the aluminum. These robust framework stuctures are not electroneutral because of the tetrahedrally incorporated trivalent aluminum, and as a result the structures must be associated with hydrogen cations and/or metallic cations. These cations are contained in the micropores of the crystal, and usually may be ion exchanged with other cations. For purposes of the present invention, the term "framework" as used herein is intended to refer only to the tetrahedrally bonded element or elements together with the associated oxygen of the robust framework, and to exclude the mobile cations that may be present. For a more detailed description of such microporous crystals, the reader is referred to "Zeolite Molecular Sieves" by D. W. Breck, Wiley, N.Y., 1974, the content of which is incorporated by reference for background.

The crystalline silicates useful herein are those having a pore size greater than 5 A.U., said pore size being evidenced by a sorption capacity of at least 2.0 wt % of cyclohexane. Such zeolites may be further subdivided into those of large pore size, such as Zeolite X, Zeolite Y, mordenite, and Zeolite Beta, and those of intermediate pore size suoh as zeolites of the ZSM-5 type more fully desoribed below. Of the large pore zeolites, Zeolite Beta is preferred because of its high activity and its high selectivity for producing methyl isopropyl ether with reduced formation of dimethyl ether. Crystalline Zeolite Beta and its conventional preparation are taught by U.S. Pat. No. 3,308,069, the entire disclosure of which is incorporated herein by reference. It has an X-ray diffraction pattern which distinguishes it from other known crystalline silicates.

The ZSM-5 type crystals are members of a novel class of zeolites that exhibit unusual properties. These zeolites have unusually low alumina contents, i.e. high silica to alumina ratios of at least 12, and they have an intracrystalline sorption capacity for normal hexane which is greater than that for water, i.e. they exhibit "hydrophobic" properties.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra.

The silica to alumina ratio referred to may be determined by conventional analysis. This ratio is meant to represent, as closely as possible, the ratio in the robust anionic framework of the zeolite crystal and to exclude aluminum in the binder or in cationic or other form within the channels.

The ZSM-5 type zeolites referred to herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the ZSM-5 type. Windows of 10-membered rings are preferred.

Rather than attempt to judge from crystal structure whether or not a zeolite possesses the necessary constrained access to molecules larger than normal paraffins, a simple determination of the "Constraint Index", or C.I., as herein defined may be made by passing continuously a mixture of an equal weight of normal hexane and 3-methylpentane over a small sample, approximately one gram or less, of mineral (in the hydrogen form) at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature is adjusted between 550° F. and 950° F. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

$$C.I. = \frac{\log \text{(fraction of n-hexane remaining)}}{\log \text{(fraction of 3-methylpentane remaining)}}$$

The Constraint Index approximates the ratio of the cracking rate constants for the two hydrocarbons. Zeolites of the ZSM-5 type have a Constraint Index of 1 to 12. C.I. values for some typical zeolites are shown in Table A.

TABLE A

| Constraint Indices of Zeolites | |
|---|---|
| CAS | C. I. |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important definition of those zeolites which are useful in the instant invention. The very nature of this parameter and the recited technique by which it is determined, however, admit of the possibility that a given zeolite can be tested under somewhat different conditions and thereby have different Constraint Indices. The Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove and found to have a Constraint Index of 1 to 12 is intended to be included in the definition regardless that the same identical zeolite tested under other defined conditions may give a Constraint Index value outside of 1 to 12.

The class of highly siliceous zeolites of intermediate pore size defined herein is exemplified by ZSM-5, ZSM-11, ZSM-12, ZSM-21, ZSM-23, ZSM-35, ZSM-38, ZSM-48, and other similar materials.

U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-21 is more particularly described in U.S. Pat. No. 4,046,859, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particulary described in U.S. Pat. No. 4,046,859, the entire content of which is incorporated herein by reference.

The specific zeolites described, when prepared in the presence of organic cations, are substantially catalytically inactive, possibly because the intra-crystalline free space is occupied by organic species from the forming solution. These organic templates are removed by heating in an inert atmosphere at 1000° F. for one hour, for example, followed by base exchange with ammonium salts followed by calcination at 1000° F. in air, which procedure converts the zeolite to the hydrogen form.

The ZSM-5 type zeolites referred to herein have a crystal framework density, in the dry hydrogen form, of not less than about 1.6 grams per cubic centimeter. The dry density for known crystal structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pycnometer techniques. For example, it may be determined by immersing the dry hydrogen form of the zeolite in an organic solvent not sorbed by the crystal. Or, the crystal density may be determined by mercury porosimetry, since mercury will fill the interstices between crystal but will not penetrate the intracrystalline free space.

The crystalline silicates described herein are preferably used in the hydrogen form, although in some instances it is contemplated that some advantage may accrue from ion-exchange with divalent or high-valent metal cations. Also, the crystals may be composited with a binder such as alumina, silica-alumina, clay, or other material used for such purpose. Such composites, in general, contain 10 to 90 wt % of zeolite, preferably 20 to 80 wt %.

What is claimed is:

1. A process for the manufacture of methyl isopropyl ether from methanol and a $C_3$ hydrocarbon fraction that contains about 20 to 100 wt % of propylene, which process comprises:

preparing a mixture of said hydrocarbon fraction and 0.1 to 10 mols of methanol per mol of propylene contained in said fraction, contacting said mixture with a solid insoluble acidic catalyst comprising materials having the structure of Zeolite Beta, said contacting being effected under a combination of conditions effective to selectively form said ether, said conditions including 1.0 to 300 atmospheres pressure, a temperature of 50° C. to about 300° C., and a WHSV of 0.5 to 50, and recovering from said contacted mixture a fraction comprising methyl isopropyl ether.

2. The process of claim 1 wherein said $C_3$ hydrocarbon fraction contains about 90 to 100 wt % propylene; wherein said mixture contains 0.5 to 2.0 mols of methanol per mol of propylene; and wherein said contacting is at a temperature of 100° C. to 210° C., a total pressure of 10 to 100 atm, and a WHSV of about 0.5 to 10.

3. The process of claim 1 wherein said zeolite is in the hydrogen form.

4. The process of claim 2 wherein said zeolite is in the hydrogen form.

* * * * *